(12) United States Patent
Ahmad et al.

(10) Patent No.: US 8,301,409 B2
(45) Date of Patent: Oct. 30, 2012

(54) PHOTON IMAGING SYSTEM FOR DETECTING DEFECTS IN PHOTOVOLTAIC DEVICES, AND METHOD THEREOF

(75) Inventors: Faisal Razi Ahmad, Niskayuna, NY (US); Oleg Sulima, Ballston Lake, NY (US); Kaustubh Ravindra Nagarkar, Clifton Park, NY (US); Ri-an Zhao, Niskayuna, NY (US); James William Bray, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 372 days.

(21) Appl. No.: 12/645,802

(22) Filed: Dec. 23, 2009

(65) Prior Publication Data

US 2011/0153228 A1 Jun. 23, 2011

(51) Int. Cl.
*G01R 29/00* (2006.01)
*G06F 11/00* (2006.01)

(52) U.S. Cl. ......... 702/132; 702/64; 702/185; 250/340; 250/200

(58) Field of Classification Search .................. None
See application file for complete search history.

(56) References Cited

U.S. PATENT DOCUMENTS

| | | | | |
|---|---|---|---|---|
| 5,693,151 A | * | 12/1997 | Kolodinski et al. | ........... 136/255 |
| 6,225,640 B1 | * | 5/2001 | Glenn et al. | ............. 250/559.45 |
| 2005/0252545 A1 | * | 11/2005 | Nowlan et al. | ................ 136/290 |
| 2008/0232083 A1 | * | 9/2008 | Xu | .................................. 362/84 |
| 2008/0264486 A1 | * | 10/2008 | Chen et al. | ..................... 136/259 |
| 2010/0201374 A1 | * | 8/2010 | Vasilyev et al. | ............... 324/538 |

FOREIGN PATENT DOCUMENTS

| | | | |
|---|---|---|---|
| EP | 1416288 A1 | * | 5/2004 |
| EP | 1840541 A1 | | 11/2005 |
| JP | 2008026113 A | | 2/2008 |
| WO | 2007128060 A1 | | 11/2007 |

OTHER PUBLICATIONS

Y. Takahashi, Y. Kaji, A. Ogane, Y. Uraoka and T. Fuyuk; ""Luminoscopy"—Novel Tool for the Diagnosis of Crystalline Silicon solar cells and Modules Utilizing Electroluminescence"; Photovoltaic Energy Conversion, Conference Record of the 2006 IEEE 4th World Conference on vol. 1, Issue , May 2006 pp. 924-927.

(Continued)

*Primary Examiner* — Hal Wachsman
(74) *Attorney, Agent, or Firm* — Paul J. DiConza

(57) ABSTRACT

A method includes supplying current to at least one photovoltaic device via a current source and detecting emitted photon radiations from the at least one photovoltaic device via a radiation detector. The method also includes outputting a signal corresponding to the detected emitted photon radiations from the radiation detector to a processor device, and processing the signal corresponding to the detected emitted photon radiations via the processor device to generate one or more two-dimensional photon images. The method further includes analyzing the one or more two-dimensional photon images to determine at least one defect in the at least one photovoltaic device.

35 Claims, 8 Drawing Sheets

OTHER PUBLICATIONS

European Search Report dated Feb. 23, 2011 and Written Opinion.
Ordaz et al., "Machine Vision for Solar Cell Characterization", Proceedings of SPIE, vol. 3966, pp. 238-248, Dec. 31, 2000, XP-002521724.
Honsberg et al., "Light Emission as a Solar Cell Analysis Technique", Solar Cells, vol. 20, No. 1, pp. 59-63, Feb. 1, 1987, XP-001109755.
Kirchartz et al., "Internal Voltages in GaInP/GainAs/Ge Multijunction Solar Cells Determined by Electroluminescence Measurements", Applied Physics Letters, vol. 92, No. 12, pp. 123502-1 to 123502-3, Mar. 24, 2008, XP-012106181.
Penner, "Electroluminescence From Silicon Devices—A Tool for Device and Material Characterization", Journal De Physique, Solid State Device Research Conference, pp. C4-797 to C4800m Sep. 13, 1988, XP-031652408.

* cited by examiner

PHOTON IMAGING SYSTEM FOR DETECTING DEFECTS IN PHOTOVOLTAIC DEVICES, AND METHOD THEREOF

BACKGROUND

The invention relates generally to photovoltaic devices, and more particularly, to an imaging system for detecting defects in photovoltaic cells, modules, and method thereof.

Solar energy is considered as an alternate source of energy relative to other forms of energy. Solar energy conversion systems are used to convert solar energy into electrical energy. The solar energy conversion system typically includes photovoltaic modules, photoelectric cells, or solar cells that convert solar energy into electrical energy for immediate use or for storage and subsequent use. Conversion of solar energy into electrical energy includes reception of light, such as sunlight, at a solar cell, absorption of sunlight into the solar cell, generation and separation of positive and negative charges creating a voltage in the solar cell, and collection and transfer of electrical charges through a terminal coupled to the solar cell.

In solar module manufacturing line, it is helpful to identify local defects, hot spots, or the like in the solar devices, for example, thin-film photovoltaic modules to predict whether the solar module is prone to degradation or whether the solar module would fail. The conventional diagnostic method used for a solar module involves exposing a finished solar module under a light source that is calibrated to sun intensity, and then measuring current as a function of the applied voltage. This conventional technique provides information related to the power conversion efficiency of the solar modules but does not provide any information about the reliability of the solar module. Moreover, substantial power is consumed for the operation of the light source.

It is desirable to have a more effective system and method to identify defects in the photovoltaic devices, for example in thin-film photovoltaic modules.

BRIEF DESCRIPTION

In accordance with one exemplary embodiment of the present invention, the method includes supplying current to at least one photovoltaic device via a current source and detecting emitted photon radiations from the at least one photovoltaic device via a radiation detector. The method also includes outputting a signal corresponding to the detected emitted photon radiations from the radiation detector to a processor device, and processing the signal corresponding to the detected emitted photon radiations via the processor device to generate one or more two-dimensional images. The method further includes analyzing the one or more two-dimensional photon images to determine at least one defect in the at least one photovoltaic device.

In accordance with another exemplary embodiment of the present invention, a system includes a current source coupled to at least one photovoltaic device and configured to supply current to the at least one photovoltaic device. A radiation detector is configured to detect emitted photon radiations from the at least one photovoltaic device and output a signal corresponding to the detected emitted photon radiations. A processor device is coupled to the radiation detector and configured to receive the signal corresponding to the detected emitted photon radiations, process the signal to generate one or more two-dimensional photon images, and analyze the one or more two-dimensional photon images to determine at least one defect in the at least one photovoltaic device.

In accordance with another exemplary embodiment of the present invention, a computer readable media to enable a processor device to determine at least one defect in the at least one photovoltaic device is disclosed.

DRAWINGS

These and other features, aspects, and advantages of the present invention will become better understood when the following detailed description is read with reference to the accompanying drawings in which like characters represent like parts throughout the drawings, wherein.

Figure 8:
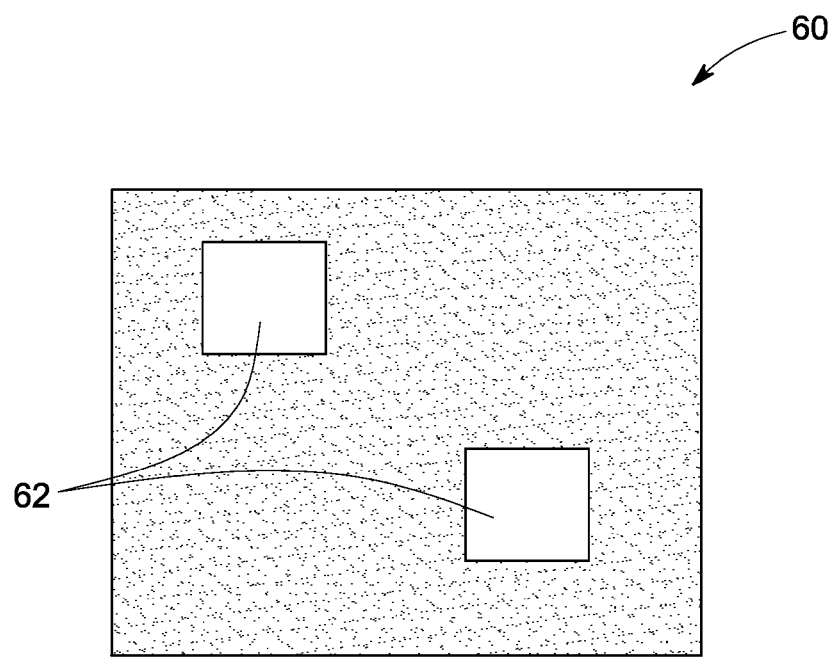
Figure 9:
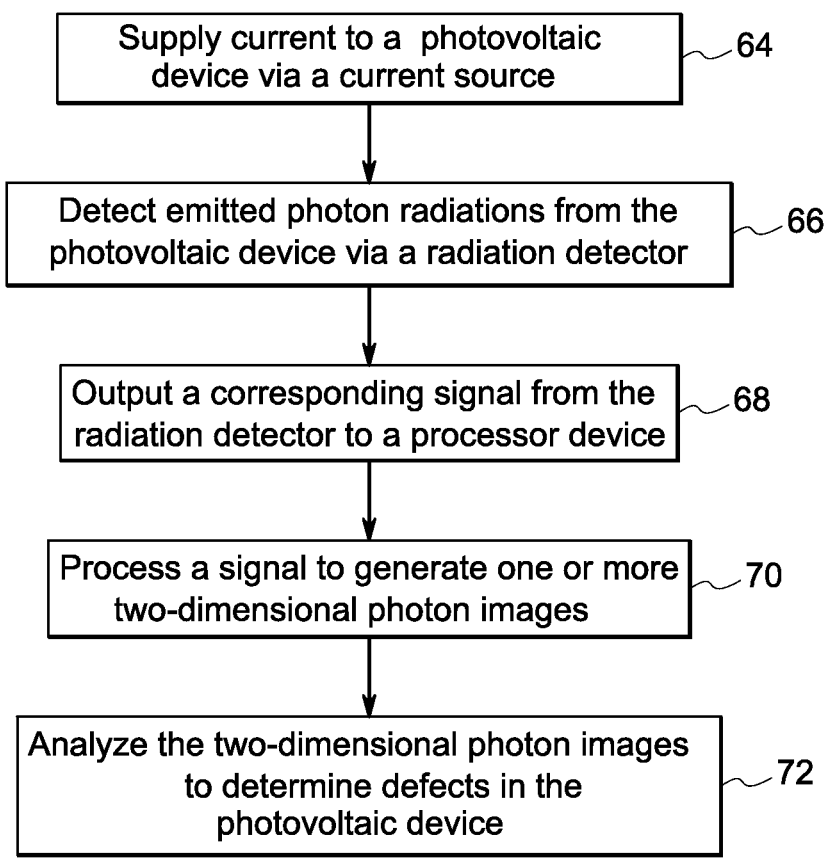

FIG. 8 is a diagrammatical representation of a two-dimensional electroluminescence image in accordance with an exemplary embodiment of the present technique; and FIG. 9 is a flow chart illustrating exemplary steps involved in the method of detecting one or more defects in a photovoltaic device, for example, a thin-film photovoltaic module in accordance with an exemplary embodiment of the present technique.

DETAILED DESCRIPTION

As discussed in detail below, embodiments of the present technique provide a diagnostic method for determining at least one defect in one or more photovoltaic device, for example a thin-film photovoltaic module. The method includes supplying current to at least one photovoltaic device via a current source and detecting emitted photon radiations from the at least one photovoltaic device via a radiation detector. The method also includes outputting a signal corresponding to the detected emitted photon radiations from the radiation detector to a processor device, and processing the signal corresponding to the detected emitted photon radiations via the processor device to generate one or more two-dimensional photon images. The method further includes analyzing the one or more two-dimensional photon images to determine at least one defect in the at least one photovoltaic device. In accordance with a specific embodiment, a diagnostic system for determining at least one defect in one or more photovoltaic device is also disclosed. In accordance with the present technique, performance and the eventual reliability of photovoltaic device can be determined from a two-dimensional photon image obtained by passing an electrical current through the photovoltaic device.

Figure 1:
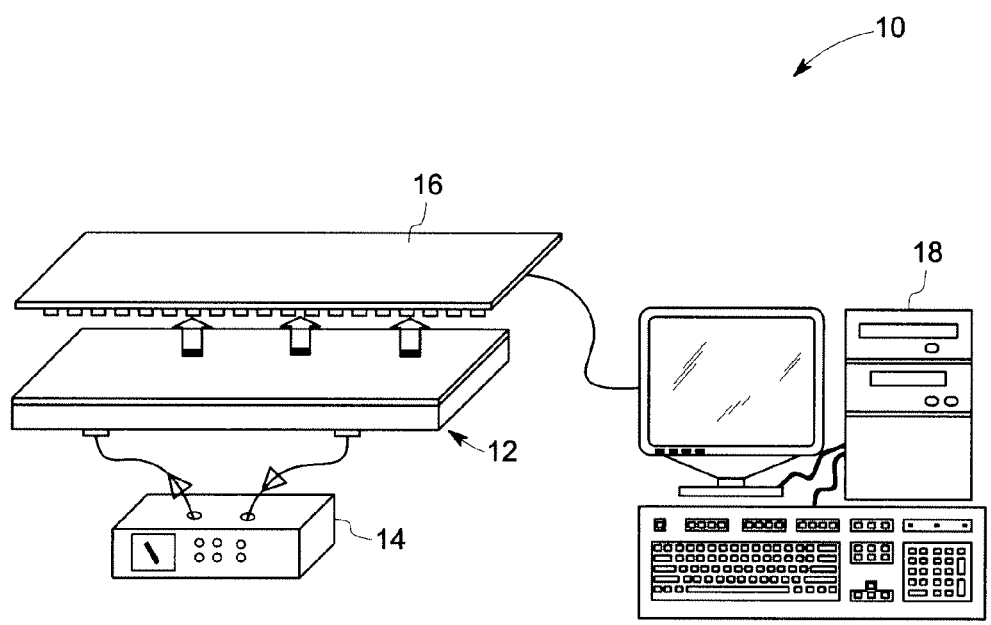
FIG. 1 is a diagrammatical representation of a system configured for diagnosing performance and reliability of a photovoltaic device, for example a thin-film photovoltaic module, in accordance with an exemplary embodiment of the present technique.

Referring to FIG. 1, a system 10 for diagnosing performance and reliability of a photovoltaic device 12, for example a thin-film photovoltaic module is disclosed. In another embodiment, the photovoltaic device 12 may be a photovoltaic cell. The thin-film photovoltaic module 12 may include cadmium telluride based photovoltaic module, copper indium gallium selenide based photovoltaic module, silicon based photovoltaic module, an amorphous silicon based thin-film photovoltaic module, or the like. It should be noted herein that other suitable photovoltaic modules, cells are also envisaged. The system 10 includes a current source 14, a radiation detector 16, and a processor device 18. The current source 14 is coupled to the thin-film photovoltaic module 12 and configured to supply current to the thin-film photovoltaic module 12. In one embodiment, the current source 14 is configured to supply current pulses to the thin-film photovoltaic module 12. In another embodiment, the current source 14 is configured to supply current to the thin-film photovoltaic module 12 for joule heating the photovoltaic module.

It is known to one skilled in the art that solar modules are devices that convert light to electric current. In the illustrated embodiment, a reverse phenomenon is observed in which the thin-film photovoltaic module 12 emits light when an electric current source is passed through the thin-film photovoltaic module 12. The reverse phenomenon may be referred to as "electroluminescence", which is the process by which light emitting diodes (LEDs) function. In other words, the thin-film photovoltaic module 12 emits photon radiations when an electric current is passed through the thin-film photovoltaic module 12. The radiation detector 16 is configured to detect photon radiations emitted from the thin-film photovoltaic module 12 and output a signal corresponding to the detected emitted photon radiations. The radiation detector 16 may be an infrared camera, charge-coupled device, or the like. It should noted herein that other suitable radiation detectors are also envisaged. The current source 14 is operated in synchronization with the operation of the radiation detector 16. In other words, when the current source 14 is activated, the radiation detector 16 is activated in synchronization with the current source 14 so as to detect the emitted photon radiations from the thin-film photovoltaic module 12.

The processor device 18 is coupled to the radiation detector 16 and configured to receive the signal corresponding to the detected emitted photon radiations from the radiation detector 16, and process the signal to generate one or more two-dimensional photon images. In one specific embodiment, the two-dimensional photon image includes a two-dimensional electroluminescence image. In another embodiment, in addition to the two-dimensional electroluminescence image, a two-dimensional thermal image may be generated using photon radiations of relatively longer wavelength emitted by joule heating the one thin-film photovoltaic module 12. The processor device 18 is further configured to analyze the one or more two-dimensional photon images to determine at least one defect in the at least one thin-film photovoltaic module 12. The defects may include cracks, voids, shunts, weak diode, local hot spots, weak or broken electrical contacts, or combinations thereof of the thin-film photovoltaic module 12. The processor device 18 will typically include hardware circuitry and software for performing computations indicative of at least one defect in the thin-film photovoltaic module 12 as described below. The processor device 18 may thus include a range of circuitry types, such as, a microprocessor based module, and application-specific or general purpose computer, programmable logic controller, or even a logical module or code within such a device.

In a specific embodiment, the processor device 18 is configured to analyze the two-dimensional photon image by correlating a two-dimensional electroluminescence image with one or more techniques including thermography, visual inspection, microscopy, or combinations thereof to determine defects in the thin-film photovoltaic module 12. In another specific embodiment, the processor device 18 is configured to analyze the two-dimensional photon image by correlating a two-dimensional electroluminescence image with results generated by accelerated life tests (solar flux based) to determine defects in the thin-film photovoltaic module 12 faster. In yet another specific embodiment, the processor device 18 is configured to analyze the two-dimensional photon image correlating a two-dimensional electroluminescence image with one or more electrical performance measurement parameters including efficiency, open circuit voltage ($V_{OC}$), short circuit current ($I_{SC}$), fill factor, or combinations thereof attributed to the thin-film photovoltaic module 12 to determine defects in the thin-film photovoltaic module 12. It should be noted herein that the term "fill factor" in the context of solar cell technology is defined as the ratio (expressed as percent) of the actual maximum obtainable power, to the theoretical obtainable power.

In the illustrated embodiment, an optical filter 20 is disposed between the thin-film photovoltaic module 12 and the radiation detector 16. The optical filter 20 is configured to transmit only the photon radiations having energy equal to a band gap of an absorber layer (not shown in FIG. 1) of the thin-film photovoltaic module 12 to the radiation detector 16. It should be noted herein that although a single thin-film photovoltaic module 12 is shown, the exemplary system and technique may be applicable for monitoring a plurality of thin-film photovoltaic modules. In other words, the exemplary system can be incorporated in any on-line manufacturing setting to monitor and control the production line. As discussed previously, in the illustrated embodiment and the subsequent embodiments, even though a thin-film photovoltaic module is discussed, the system 10 is also applicable to other photovoltaic devices.

Figure 2:
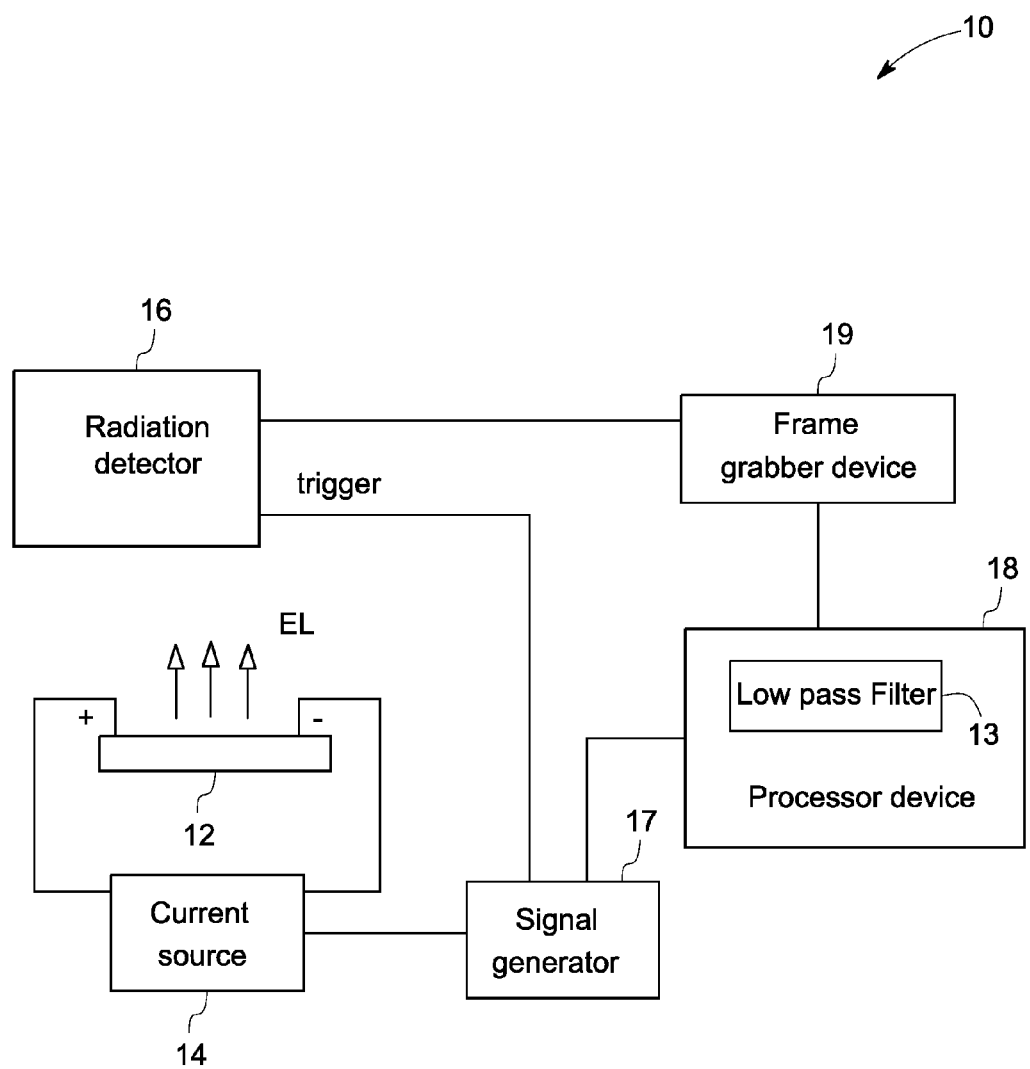
FIG. 2 is a more detailed diagrammatical representation of a system configured for diagnosing performance and reliability of a photovoltaic device, for example a thin-film photovoltaic module in accordance with an exemplary embodiment of the present technique.

Referring to FIG. 2, a more detailed representation of the system 10 is disclosed. As discussed above, the current source 14 is coupled to the thin-film photovoltaic module 12 and configured to supply current to the thin-film photovoltaic module 12. The radiation detector 16 is configured to detect photon radiations emitted from the thin-film photovoltaic module 12 and output a signal corresponding to the detected emitted photon radiations. In the illustrated embodiment, a voltage bias waveform to the module 12 is modulated via a signal generator 17. The signal generator 17 is also configured to transmit a synchronous trigger signal to the radiation detector 16. The processor device 18 is coupled to the radiation detector 16 via a frame grabber device 19. The processor device 18 is configured to receive the signal corresponding to the detected emitted photon radiations from the radiation detector 16 via the frame grabber device 19, and process the signal to generate one or more two-dimensional photon images.

It should be noted herein that since electroluminescence generated by photovoltaic devices is generally weak and are subjected to the influence of background scattering light, an increase in integration time constants of the radiation detector 16 is not sufficient to generate a clean electroluminescence image. In one embodiment, in order to obtain a background free electroluminescence image ("clean electroluminescence image"), a technique referred to as "lock-in electroluminescence detection technique" is used. In such a technique, the module 12 is activated by periodically modulated bias, and synchronous electroluminescence image detection is enabled. The electroluminescence image is processed digitally using low-pass filters 13, for enabling detection of weak signals. The lock-in electroluminescence intensity is determined by the following relation:

$$S(x, y) = \sum_{i=1}^{N} I(x, y, t_i)\sin(\omega_v t_i - \varphi_s) \quad (1)$$

where "S" is the lock-in electroluminescence intensity, (x,y) are the location coordinates, I(t) is the electroluminescence intensity per image, "t" is the time, $\omega_v$ is the bias angular frequency (modulation frequency), $\phi_S$ is the system phase shift, "N" is the total number of electroluminescence images.

As discussed previously, the modulated electroluminescence image stream is filtered using low-pass filters 13 to reject the broadband noise except electroluminescence signal near to the modulation frequency $\omega_v$. The detection frame rate ($\omega_f = 1/2\pi\Delta t$) is set higher than the modulation frequency $\omega_v$ so as to increase the detection accuracy. The system phase shift $\phi_S$ may be determined by measuring a light emitting diode instead of the module 12, or tuned in real time to maximize the electroluminescence intensity.

Figure 3:
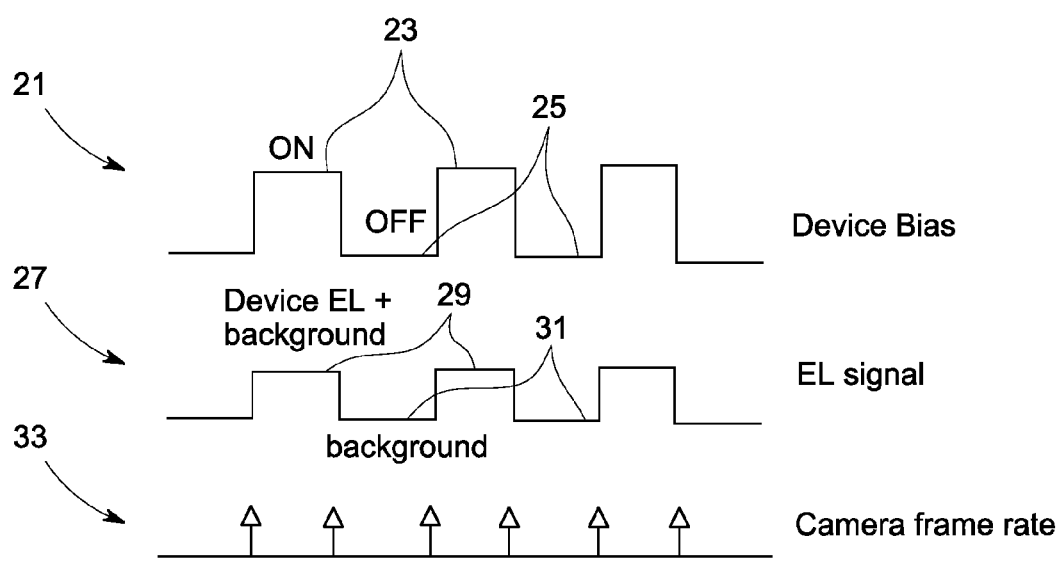
FIG. 3 is a diagrammatical representation of a dual rate electroluminescence detection technique for obtaining a background free electroluminescence image ("clean electroluminescence image") in accordance with an exemplary embodiment of the present technique.

Referring to FIG. 3, a technique referred to as "Dual rate electroluminescence detection technique" for obtaining a background free electroluminescence image ("clean electroluminescence image") is disclosed. Reference numeral 21 is representative of the module bias signal having peak regions 23 and low regions 25. The peak regions 23 indicate "ON state" of the module bias cycle and low regions 25 indicate "OFF state" of the module bias cycle. Reference numeral 27 is representative of the electroluminescence signal having peak regions 29 and low regions 31. The peak regions 29 indicate collection of the electroluminescence image signal and the background image signal during "ON state" of the module bias cycle and the low regions 31 indicate collection of background image signal during "OFF state" of the module bias cycle. Reference numeral 33 is representative of the detection frame rate.

In such a technique, the module is activated by periodically modulated bias, and synchronous electroluminescence image detection is enabled. In the dual rate electroluminescence detection technique, the detection frame rate is set twice that of the module voltage bias. The background image signal is subtracted from the electroluminescence signal to obtain a clean electroluminescence image. The background free images may be averaged over a plurality of frames. The module bias voltage rate depends upon the optimized detector integration time. Such a technique enables faster and real time detection of electroluminescence image even in the presence of varying background light. The dual rate electroluminescence detection technique is also immune to the variations in background images since the background images are subtracted dynamically.

With reference to embodiments discussed with respect to FIGS. 2 and 3, signal-to-noise ratio is enhanced based on the detection frame rate and measurement time. The processing of the electroluminescence may be done using digital signal process (DSP) hardware for enhancing the speed of image processing. Alternatively, the image subtraction process in dual-rate electroluminescence detection technique may be performed using an on-camera memory.

Figure 4:
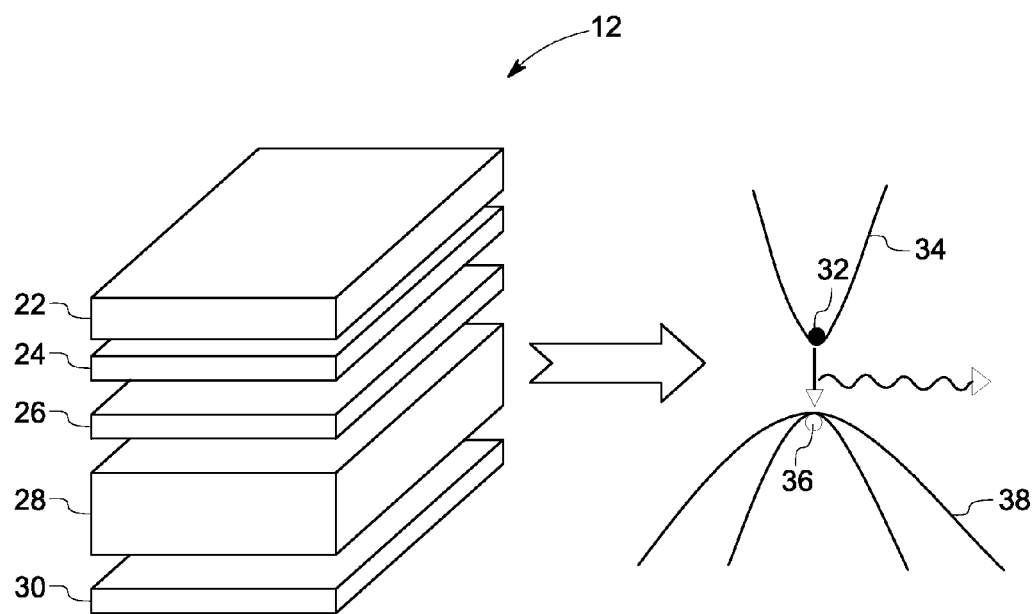
FIG. 4 is a diagrammatical representation of a photovoltaic device, for example, a thin-film photovoltaic module in accordance with an exemplary embodiment of the present technique.

Referring to FIG. 4, a thin-film photovoltaic module 12 in accordance with an exemplary embodiment of the present invention is illustrated. The module 12 includes a glass layer 22, a transparent conductive oxide layer 24, an n-type cadmium sulfide layer 26, a p-type cadmium telluride layer 28 (generally referred to as "absorber layer"), and a back-contact layer 30. The p-type cadmium telluride layer 28 absorbs the light photons and generates free electrons. The n-type cadmium sulfide layer 26 emits these free electrons through the layers 22, 24 into an outer circuit (not shown). The electrons return into the p-type cadmium telluride layer 28 to recombine with holes through the back contact layer 30. In other words, an electron 32 in a conduction band 34 recombines with a hole 36 in a valence band 38 generating energy as a photon. As discussed above, in the illustrated embodiment, a reverse phenomenon is observed in which the thin-film photovoltaic module 12 emits light when an electric current source is passed through the thin-film photovoltaic module 12. In other words, the thin-film photovoltaic module 12 emits photon radiations when an electric current source is passed through the thin-film photovoltaic module 12. It should be noted herein that the illustrated module 12 is an exemplary embodiment and the configuration of the thin-film photovoltaic module should not be construed as limiting.

The conventional diagnostic method used for a solar module involves exposing a finished solar module under a light source that is calibrated to sun intensity, and then measuring current as a function of the applied voltage. This conventional technique provides information related to the power conversion efficiency of the solar modules but does not provide any information about the reliability of the solar module. Moreover, substantial power is consumed for the operation of the light source.

In accordance with an exemplary embodiment of the present invention, the processor device 18 (shown in FIG. 1) processes the signal corresponding to the detected emitted photon radiations from the radiation detector to generate one or more two-dimensional photon images representative of the thin-film photovoltaic module 12. For example, the generated two-dimensional electroluminescence image is representative of an entire surface of the thin-film photovoltaic module 12 and can be analyzed to identify at least one defect of the thin-film photovoltaic module 12. Detection of local defects, hot spots, or the like of the thin-film photovoltaic module may be indicative of potential failures of the module. A list of defects may be identified by studying the two-dimensional photon images. As a result, it is possible to predict whether the module is prone to failure or degradation.

Figure 5:
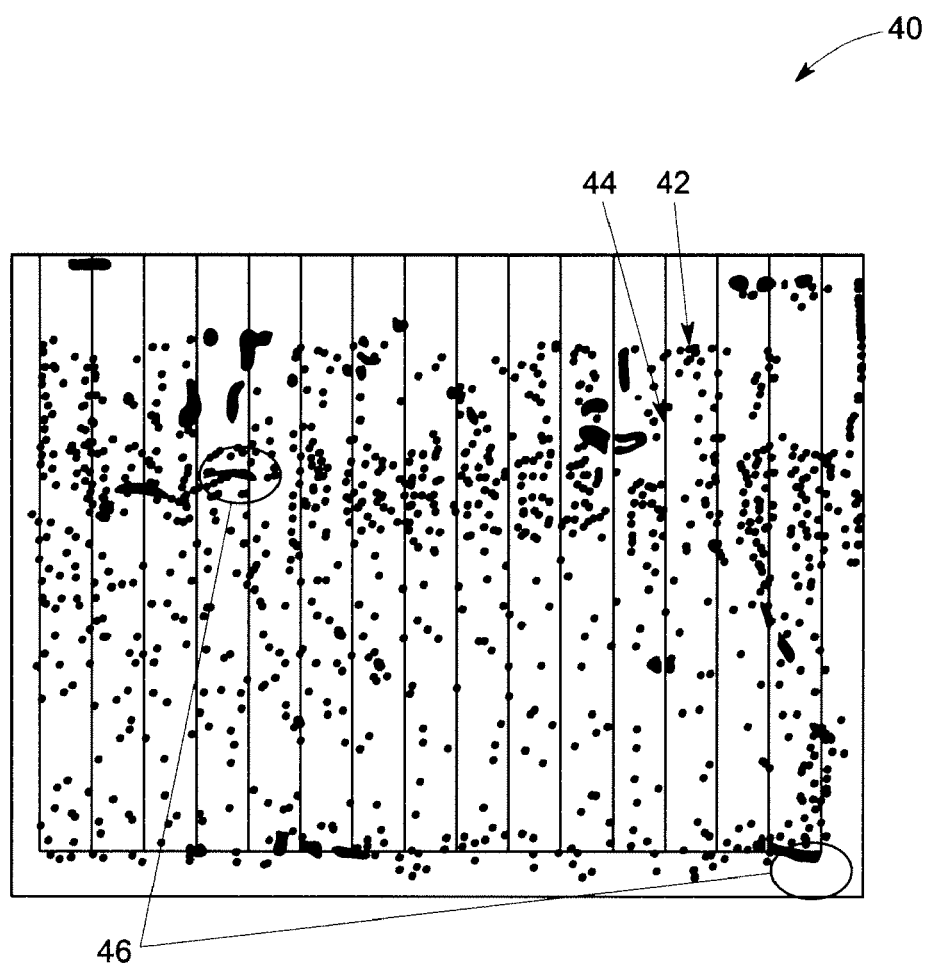
FIG. 5 is a diagrammatical representation of a two-dimensional electroluminescence image representative of an entire surface of a photovoltaic device, for example a thin-film photovoltaic module in accordance with an exemplary embodiment of the present technique.

Referring to FIG. 5, a two-dimensional electroluminescence image 40 representative of an entire surface of a thin-film photovoltaic module is illustrated. As discussed above, the processor device is configured to receive the signal corresponding to the detected emitted photon radiations from the radiation detector, and process the signal to generate one or more two-dimensional photon images. The processor device 18 is further configured to analyze the one or more two-dimensional photon images to determine at least one defect in the thin-film photovoltaic module.

In the illustrated embodiment, the two-dimensional electroluminescence image 40 shows variation in performance of the module across a surface of the module. A plurality of brighter regions represented by reference numeral 42 of the electroluminescence image 40 is representative of regions of relatively higher efficiency in the module. In other words, the regions 42 are indicative of regions of the module that convert solar light into electricity at higher efficiency. A plurality of dark lines represented by reference numeral 44 of the electroluminescence image 40 is indicative of a plurality of grid lines of the thin-film photovoltaic module. The grid lines of the module are current collection lines typically including screen-printed silver epoxy coated on the module. It should be noted herein that grid lines of the module block sunlight and electroluminescence. Hence grid lines are represented by the plurality of dark lines 44. A plurality of darker regions represented by reference numeral 46 of the electroluminescence image 40 is representative of regions of defect in the module. In other words, the regions 46 are indicative of regions that convert solar light into electricity at lower efficiency. The defects may include cracks, voids, shunts, weak diode, local hot spots, weak or broken electrical contacts, or combinations thereof of the thin-film photovoltaic module.

Figure 6:
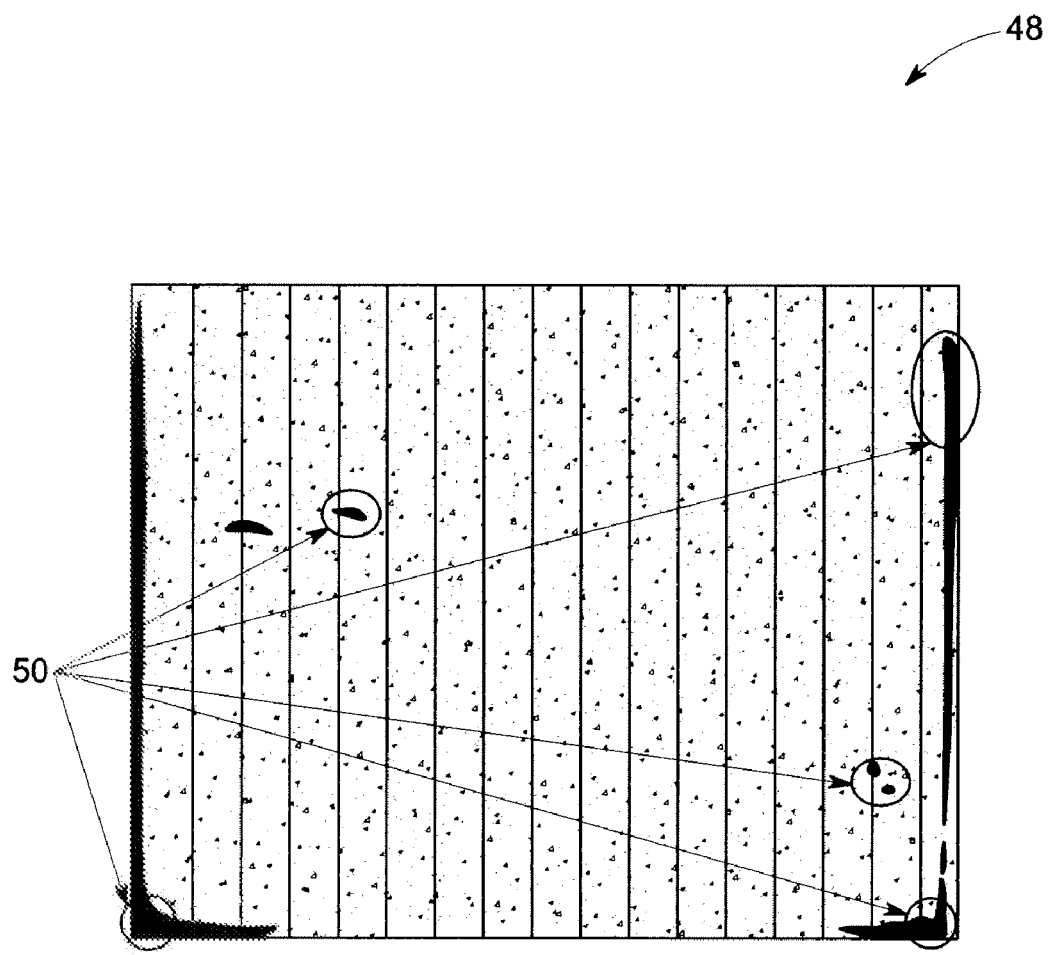
FIG. 6 is a diagrammatical representation of a two-dimensional thermal image representative of an entire surface of a photovoltaic device, for example a thin-film photovoltaic module in accordance with an exemplary embodiment of the present technique.

Referring to FIG. 6, a two-dimensional thermal image 48 representative of an entire surface of a thin-film photovoltaic module is illustrated. As discussed above, in addition to a two-dimensional electroluminescence image, the two-dimensional thermal image 48 may be generated using photon radiations of relatively longer wavelength emitted by joule heating the one thin-film photovoltaic module. Thus different regions in the photon radiation spectrum could provide complementary information pertaining to the thin-film photovoltaic module. In the illustrated embodiment, the two-dimensional thermal image 40 provides complementary information indicative of variation in performance of the module across a surface of the module. A plurality of brighter regions represented by reference numeral 50 of the thermal image 48 is representative of regions of defect in the module.

Figure 7:
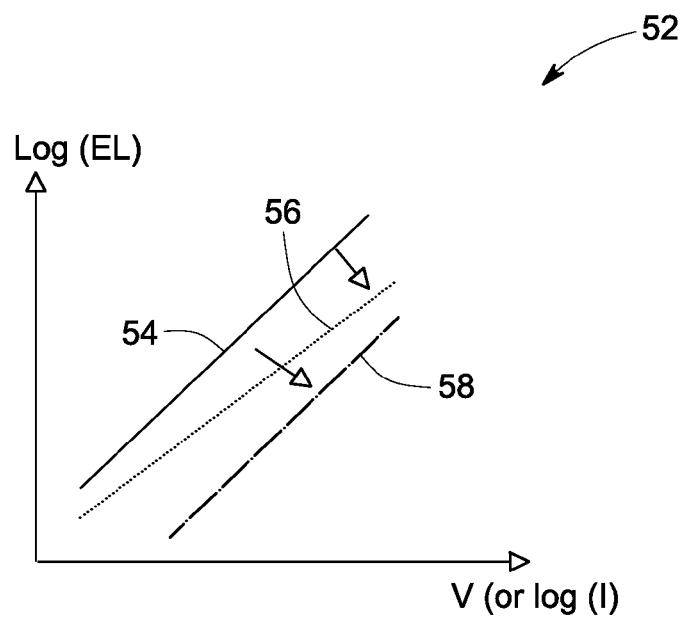
FIG. 7 is a graph illustrating variation in electroluminescence intensity with respect to applied current or voltage in accordance with an exemplary embodiment of the present technique.

Referring to FIG. 7, a graph 52 illustrating variation in electroluminescence intensity from a particular region of a two-dimensional electroluminescence image with respect to applied current or voltage is illustrated. In one embodiment, the logarithm of electroluminescence intensity (log EL) is represented by the Y-axis and applied voltage (V) is represented by the X-axis. In one such embodiment, the current source is configured to forward bias the thin-film photovoltaic module with higher current density. For example, the higher current density may be in the range of one to hundred mA/cm$^2$ (milliamps per centimeter square). In the illustrated embodiment, electroluminescence intensity from a reference region of the thin-film photovoltaic module is represented by a solid line 54, electroluminescence intensity from a region with increased series resistance (Rs) of the module is represented by a dashed line 56, and electroluminescence intensity from a region with decreased shunt resistance (Rsh) of the module is represented by a dashed line 58.

When a forward bias is applied to the module with higher current density, the electroluminescence intensity distribution of the two-dimensional electroluminescence image is modulated by the series resistance and the shunt resistance. Hence by analyzing variation in electroluminescence intensity distribution of the two-dimensional electroluminescence image with respect to applied voltage, the two-dimensional electroluminescence image can be converted to two-dimensional images of series resistance and the shunt resistance. It should be noted herein that the electroluminescence intensity depends on a local diode voltage exponentially. Hence, shunt resistance decrease 58 shifts downward the electroluminescence-voltage curve with respect to the reference electroluminescence 54, and series resistance increase 56 changes the slope of electroluminescence-voltage curve with respect to the reference electroluminescence 54. Such series resistance change 56 and the shunt resistance change 58 maps may be generated by measuring electroluminescence intensity at a plurality of voltage values. In another embodiment, similar maps may be generated by plotting variation of the logarithm of electroluminescence intensity (log EL) with respect to logarithm of current.

Referring to FIG. 8, a two-dimensional electroluminescence image 60 is illustrated. In one such embodiment, the current source is configured to forward bias a thin-film photovoltaic module with lower current density. For example, the lower current density may in the range of 0.1 to 10 mA/cm2 (milliamps per centimeter square). When forward bias is applied to the module with lower current density, a series resistance of the module can be neglected since the voltage drop is relatively small. In such an embodiment, it is possible to detect defects such as non-uniformity in an absorber layer of the module. It should be noted herein that any non-uniformity in the absorber layer of the module results in a variation in diode "turn-on voltage" (above which substantial current flow into the diode) of the module. Regions of the module having lower diode "turn-on voltage" allow higher current to flow. In other words, such regions have relatively higher local current injection levels. As discussed previously, since the electroluminescence intensity depends on a current density locally, variation in local diode turn-on voltage results in a two-dimensional electroluminescence image having higher contrast. In the illustrated embodiment, one or more brighter regions 62 of the image 60 corresponds to regions with lower diode "turn-on voltage"/weak diode.

In accordance with a specific embodiment, "a micro electroluminescence technique" is employed to determine at least one defect in the at least one photovoltaic cell. In such an embodiment, the photovoltaic cell is a light emitting diode. In one such embodiment, the current source is configured to forward bias the photovoltaic cell at a predetermined voltage. The radiation detector detects photon radiations emitted from the junction regions of the photovoltaic cell and output a signal corresponding to the detected emitted photon radiations. The radiation detector has spatial resolution compatible with the features required to examine junction regions of the photovoltaic cell. In one embodiment, the radiation detector may have a resolution of the order of grain size (for example, micron) required to examine grain boundaries at the junction regions of the photovoltaic cell. The radiation detector may be an infrared microscope. The microscopic portions of the junction regions of the photovoltaic cell important for the electroluminescence emission may be determined by examining the magnitude of electroluminescence photon emission with fine spatial resolution. Such microscopic portions of the junction regions are important for photovoltaic action. The performance of the photovoltaic cell may be enhanced by increasing portions of the junction regions of the photovoltaic cell found to be most efficacious in electroluminescence and decreasing those junction regions found not to contribute to electroluminescence.

Referring to FIG. 9, a flow chart illustrating exemplary steps involved in the method of detecting one or more defects in a photovoltaic device, for example a thin-film photovoltaic module is disclosed. The method includes supplying current to a thin-film photovoltaic module via a current source as represented by the step 64. In one embodiment, current pulses are supplied to the thin-film photovoltaic module. In another embodiment, the current is supplied to the thin-film photovoltaic module for joule heating the photovoltaic module.

In the illustrated embodiment, a reverse phenomenon is observed in which the thin-film photovoltaic module emits light when an electric current is passed through the thin-film photovoltaic module. The reverse phenomenon may be referred to as "electroluminescence". The thin-film photovoltaic module emits photon radiations when an electric current source is passed through the thin-film photovoltaic module. Photon radiations emitted from the thin-film photovoltaic module are detected via a radiation detector as represented by the step 66. The radiation detector may be an infrared camera, charge-coupled device, or the like. The detector outputs a signal corresponding to the detected emitted photon radiations to a processor device as represented by the step 68. The current source is operated in synchronization with the operation of the radiation detector. In other words, when the current source is activated, the radiation detector is activated in synchronization with the current source so as to detect the emitted photon radiations from the thin-film photovoltaic module. In the illustrated embodiment, only the photon radiations having energy equal to a band gap of an absorber layer of the thin-film photovoltaic module is transmitted to the radiation detector via an optical filter disposed between the thin-film photovoltaic module and the radiation detector.

The method further includes receiving the signal corresponding to the detected emitted photon radiations from the radiation detector, and processing the signal to generate one or more two-dimensional photon images as represented by the step 70. In one specific embodiment, the two-dimensional photon image includes a two-dimensional electroluminescence image. In another embodiment, in addition to the two-dimensional electroluminescence image, a two-dimensional thermal image may be generated using photon radiations of relatively longer wavelength emitted by joule heating the one thin-film photovoltaic module. The method further includes analyzing the one or more two-dimensional photon images to determine at least one defect in the thin-film photovoltaic module as represented by the step 72. The defects may include cracks, voids, shunts, weak diode, local hot spots, weak or broken electrical contacts, or combinations thereof of the thin-film photovoltaic module.

In one specific embodiment, the thin film photovoltaic module is forward biased with higher current density and relationship between a two-dimensional electroluminescence image intensity with respect to applied voltage is analyzed to generate a series resistance map, a shunt resistance map, or combinations thereof to determine defects in the thin-film photovoltaic module. In another specific embodiment, relationship between two-dimensional electroluminescence image intensity with respect to applied current is similarly analyzed to determine defects in the thin-film photovoltaic module. In another embodiment, the thin-film photovoltaic module is forward biased with lower current density and contrast in intensity of the generated two-dimensional electroluminescence image is analyzed to determine defects in the thin-film photovoltaic module.

It should be noted herein that the exemplary electroluminescence technique facilitates capturing a two-dimensional electroluminescence image corresponding to the entire module via an infrared camera or CCD device thus eliminating the conventional need of moving a probe on a surface of the thin-film photovoltaic module as in the case of using a Light Beam Induced Current (LBIC) instrument. Also, the exemplary electroluminescence technique is more energy efficient than a conventional solar simulator tester, which consumes a lot of power for operation of a light source. The exemplary electroluminescence technique may be applicable for monitoring photovoltaic device manufacturing process, handling of the photovoltaic devices during shipping and installation, and effect of one or more elements on installed photovoltaic devices.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method comprising:
supplying current to at least one photovoltaic device via a current source;
transmitting only photon radiations having energy equal to a band gap of an absorber layer of the at least one photovoltaic device, from the at least one photovoltaic device to a radiation detector via an optical filter disposed between the at least one photovoltaic device and the radiation detector;
detecting the emitted photon radiations from the at least one photovoltaic device via the radiation detector;
outputting a signal corresponding to the detected emitted photon radiations from the radiation detector to a processor device;
processing the signal corresponding to the detected emitted photon radiations via the processor device to generate one or more two-dimensional photon images; and
analyzing variation in electroluminescence intensity distribution of the one or more two-dimensional photon images to determine at least one defect in the at least one photovoltaic device.

2. The method of claim 1, wherein supplying current comprises supplying current pulses to the at least one photovoltaic device.

3. The method of claim 1, further comprising synchronizing the operation of the current source with the operation of the radiation detector.

4. The method of claim 1, further comprising supplying current to the at least one photovoltaic device for joule or thermal heating the at least one photovoltaic device.

5. The method of claim 1, wherein the one or more two-dimensional photon images comprises a two-dimensional electroluminescence image, a two-dimensional thermal image, or combinations thereof.

6. The method of claim 1, wherein the defect comprises cracks, voids, shunts, weak diode, local hot spots, weak or broken electrical contacts, or combinations thereof.

7. The method of claim 1, wherein supplying current to the at least one photovoltaic device comprises forward biasing the at least one photovoltaic device with higher current density.

8. The method of claim 7, wherein analyzing variation in electroluminescence intensity distribution of the one or more two-dimensional photon images comprises analyzing variation in electroluminescence intensity distribution of the two-dimensional electroluminescence image with respect to an applied voltage to generate a series resistance map, a shunt resistance map, or combinations thereof to determine the at least one defect in the at least one photovoltaic device.

9. The method of claim 7, wherein analyzing variation in electroluminescence intensity distribution of the one or more two-dimensional photon images comprises analyzing variation in electroluminescence intensity distribution of the two-dimensional electroluminescence image with respect to the applied current to generate a series resistance map, a shunt resistance map, or combinations thereof to determine the at least one defect in the at least one photovoltaic device.

10. The method of claim 1, wherein supplying current to at least one photovoltaic device comprises forward biasing the at least one photovoltaic device with lower current density.

11. The method of claim 10, wherein analyzing variation in electroluminescence intensity distribution of the one or more two-dimensional photon images comprises analyzing contrast in intensity of the two-dimensional electroluminescence image to determine the at least one defect in the at least one photovoltaic device.

12. The method of claim 1, wherein processing the signal comprises using a lock-in electroluminescence image detection technique to generate a background free two-dimensional photon image.

13. The method of claim 12, further comprising digitally processing the two-dimensional photon image using one or more low-pass filters.

14. The method of claim 1, wherein processing the signal comprises using a dual rate electroluminescence image detection technique to generate a background free two-dimensional photon image.

15. The method of claim 14, wherein the dual rate electroluminescence image detection technique comprises setting detection frame rate twice that of photovoltaic device voltage bias.

16. The method of claim 1, wherein analyzing variation in electroluminescence intensity distribution of the two-dimensional photon images comprises correlating the two-dimensional electroluminescence image with one or more techniques comprising thermography, visual inspection, microscopy, accelerated life test, or combinations thereof.

17. The method of claim 1, wherein analyzing variation in electroluminescence intensity distribution of the two-dimensional photon images comprises correlating the two-dimensional electroluminescence image with one or more electrical performance measurement parameters comprising efficiency, open circuit voltage, short circuit current, fill factor, or combinations thereof attributed to the photovoltaic device.

18. The method of claim 1, wherein analyzing variation in electroluminescence intensity distribution of the one or more two-dimensional photon images comprises a micro electroluminescence technique.

19. A system comprising:
  a current source coupled to at least one photovoltaic device and configured to supply current to the at least one photovoltaic device,
  a radiation detector configured to detect emitted photon radiations from the at least one photovoltaic device and output a signal corresponding to the detected emitted photon radiations,
  an optical filter disposed between the at least one photovoltaic device and the radiation detector and configured to transmit only the photon radiations having energy equal to a band gap of an absorber layer of the at least one photovoltaic device to the radiation detector; and
  a processor device coupled to the radiation detector and configured to receive the signal corresponding to the detected emitted photon radiations, process the signal to generate one or more two-dimensional photon images, and analyze the variation in electroluminescence intensity distribution of one or more two-dimensional photon images to determine at least one defect in the at least one photovoltaic device.

20. The system of claim 19, wherein the current source is configured to supply current pulses to the at least one photovoltaic device.

21. The system of claim 19, wherein the current source is operated in synchronization with the operation of the radiation detector.

22. The system of claim 19, wherein the current source is configured to supply the current to the at least one photovoltaic device for joule heating the at least one photovoltaic device.

23. The system of claim 19, wherein the one or more two-dimensional photon images comprises a two-dimensional electroluminescence image, a two-dimensional thermal image, or combinations thereof.

24. The system of claim 19, wherein the defect comprises cracks, voids, shunts, weak diode, local hot spots, weak or broken electrical contacts, or combinations thereof.

25. The system of claim 19, wherein the current source is configured to forward bias the at least one photovoltaic device with higher current density.

26. The system of claim 19, wherein the processor device is configured to analyze variation in electroluminescence intensity distribution of the two-dimensional electroluminescence image with respect to an applied voltage to generate a series resistance map, a shunt resistance map, or combinations thereof to determine the at least one defect in the at least one photovoltaic device.

27. The system of claim 19, wherein the processor device is configured to analyze variation in electroluminescence intensity distribution of the two-dimensional electroluminescence image with respect to the applied current to generate a series resistance map, a shunt resistance map, or combinations thereof to determine the at least one defect in the at least one photovoltaic device.

28. The system of claim 19, wherein the current source is configured to forward bias the at least one photovoltaic device with lower current density.

29. The system of claim 28, wherein the processor device is configured to analyze contrast in intensity of the two-dimensional electroluminescence image to determine the at least one defect in the at least one photovoltaic device.

30. The system of claim 28, wherein the photovoltaic device comprises a silicon based photovoltaic module, or a cadmium telluride based thin-film photovoltaic module, or a copper indium gallium selenide based thin-film photovoltaic module, or an amorphous silicon based thin-film photovoltaic module.

31. The system of claim 19, wherein the processor device is configured to process the signal using a lock-in electroluminescence image detection technique to generate a background free two-dimensional photon image.

32. The system of claim 31, wherein the processor device is configured to digitally process the two-dimensional photon image using one or more low-pass filters.

33. The system of claim 19, wherein the processor device is configured to process the signal using a dual rate electroluminescence image detection technique to generate a background free two-dimensional photon image.

34. The system of claim 33, wherein a detection frame rate is set twice that of photovoltaic device voltage bias.

35. A non-transitory computer readable media to enable a processor device to determine at least one defect in at least one photovoltaic device, the computer readable media comprising:
  routines for transmitting only photon radiations having energy equal to a band gap of an absorber layer of the at least one photovoltaic device, from the at least one photovoltaic device to a radiation detector via an optical filter disposed between the at least one photovoltaic device and the radiation detector;

routines for detecting the emitted photon radiations from the at least one photovoltaic device via the radiation detector, routines for outputting a signal corresponding to the detected emitted photon radiations from the radiation detector to the processor device;

routines for processing the signal corresponding to the detected emitted photon radiations via the processor device to generate one or more two-dimensional photon images; and routines for analyzing variation in electroluminescence intensity distribution of the one or more two-dimensional photon images to determine at least one defect in the at least one photovoltaic device.

* * * * *